US012220145B2

(12) United States Patent
Jamous et al.

(10) Patent No.: US 12,220,145 B2
(45) Date of Patent: Feb. 11, 2025

(54) DEBULKING CATHETER

(71) Applicant: Medtronic Vascular, Inc., Santa Rosa, CA (US)

(72) Inventors: Aram Jamous, Athenry (IE); Alan Ryan, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 431 days.

(21) Appl. No.: 17/682,595

(22) Filed: Feb. 28, 2022

(65) Prior Publication Data
US 2022/0304720 A1 Sep. 29, 2022

Related U.S. Application Data

(60) Provisional application No. 63/167,627, filed on Mar. 29, 2021.

(51) Int. Cl.
*A61B 17/3207* (2006.01)
*A61B 17/32* (2006.01)
*A61B 17/3205* (2006.01)

(52) U.S. Cl.
CPC ......... *A61B 17/320758* (2013.01); *A61B 17/32002* (2013.01); *A61B 17/32053* (2013.01); *A61B 2017/320775* (2013.01)

(58) Field of Classification Search
CPC .. A61B 17/320758; A61B 2017/00199; A61B 2017/0042; A61B 2017/00526; A61B 2017/00964; A61B 2017/320004; A61B 2017/00336; A61B 2017/00398; A61B 2017/00477; A61B 2017/00876; A61B 2017/22049
See application file for complete search history.

(56) References Cited

U.S. PATENT DOCUMENTS

| | | | |
|---|---|---|---|
| 7,172,610 B2 | 2/2007 | Heitzmann et al. | |
| 8,579,926 B2 | 11/2013 | Pintor et al. | |
| RE45,638 E | 8/2015 | Tartaglia et al. | |
| 9,314,263 B2 | 4/2016 | Escudero et al. | |
| 2009/0222023 A1* | 9/2009 | Boone, III | A61B 17/545 606/131 |
| 2014/0058423 A1 | 2/2014 | Smith et al. | |
| 2016/0136788 A1 | 5/2016 | Nashimoto | |
| 2016/0331645 A1* | 11/2016 | Bagwell | A61J 15/0026 |
| 2017/0196620 A1 | 7/2017 | Jadhav | |
| 2019/0262034 A1* | 8/2019 | Spangler | A61B 17/320758 |
| 2020/0107898 A1* | 4/2020 | Kim | A61B 1/0016 |
| 2020/0155194 A1* | 5/2020 | Schneider | A61B 17/320725 |
| 2023/0071306 A1* | 3/2023 | Miller | A61B 5/6852 |

FOREIGN PATENT DOCUMENTS

| | | |
|---|---|---|
| AU | 2009240503 B2 | 10/2009 |
| WO | 2010056714 A1 | 5/2010 |

OTHER PUBLICATIONS

International Search Report and Written Opinion for PCT/IB2022/05295, Jun. 2, 2022, 12 pages, Rijiswijk, Netherlands.

* cited by examiner

*Primary Examiner* — Shaun L David
*Assistant Examiner* — Rachael L Geiger
(74) *Attorney, Agent, or Firm* — Stinson LLP (57) ABSTRACT

A debulking catheter includes an advancer for advancing a tissue-removing element, and a linear-force indicator. The linear-force indicator provides feedback to the user based on an amount of linear force being applied to the advancer.

20 Claims, 8 Drawing Sheets

DEBULKING CATHETER

FIELD

The present technology is generally related to a debulking catheter for debulking a body lumen.

BACKGROUND

Debulking catheters are used to remove unwanted tissue in body lumens. As an example, atherectomy catheters are used to remove tissue from a blood vessel to open the blood vessel and improve blood flow through the vessel. Atherectomy catheters typically abrade, cut, excise, ablate or otherwise remove the unwanted tissue.

SUMMARY

In one aspect, the present disclosure provides a debulking catheter for debulking a body lumen. The debulking catheter comprises a catheter body extending distally from the handle and configured to be inserted into the body lumen. The catheter body has a length and includes a drive shaft extending along the length of the catheter body. The drive shaft is configured to be rotated about its longitudinal axis. A tissue-removing element is coupled to and configured to be rotated by the drive shaft. The tissue-removing element is configured to remove tissue from the body lumen as it is rotated by the drive shaft. A handle is operatively coupled to a proximal end of the catheter body. The handle includes a drive operatively coupled to the drive shaft and configured to impart rotation of the drive shaft about its longitudinal axis. An advancer of the handle is operatively coupled to the drive to selectively translate the drive together with the drive shaft and the burr to linearly advance and retract the drive shaft and the burr relative to the handle. A linear-force indicator of the handle is configured to provide feedback to the user indicating an amount of linear force being applied to the advancer.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 13:
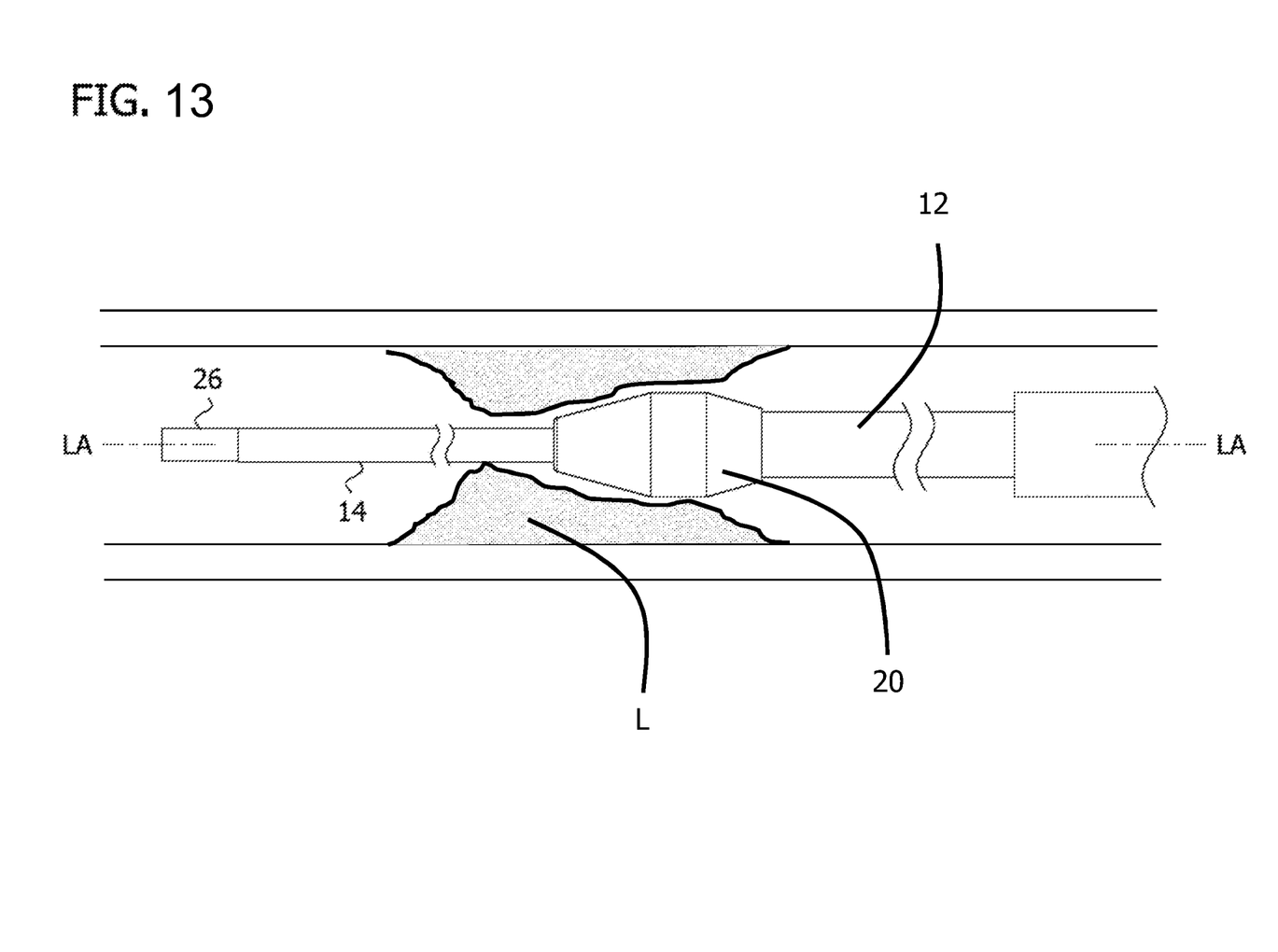
FIG. 13 is a schematic illustration of the distal end portion of the catheter received in a body lumen, such as a blood vessel, and engaging a lesion in the body lumen.

The present disclosure relates to a rotational debulking catheter for removing tissue in a body lumen. As an example, the rotational debulking catheter is suitable for use as rotational atherectomy device for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a blood vessel wall (e.g., coronary arterial wall, venous wall etc.), such as shown in FIG. 13. The catheter may be used to facilitate percutaneous coronary angioplasty (PTCA) or the subsequent delivery of a stent. Features of the disclosed embodiments may also be suitable for treating chronic total occlusion (CTO) of blood vessels. The features of the disclosed embodiments are not limited to treatment of blood vessels. For example, the disclosed features may also be used for treating stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

Figure 1:
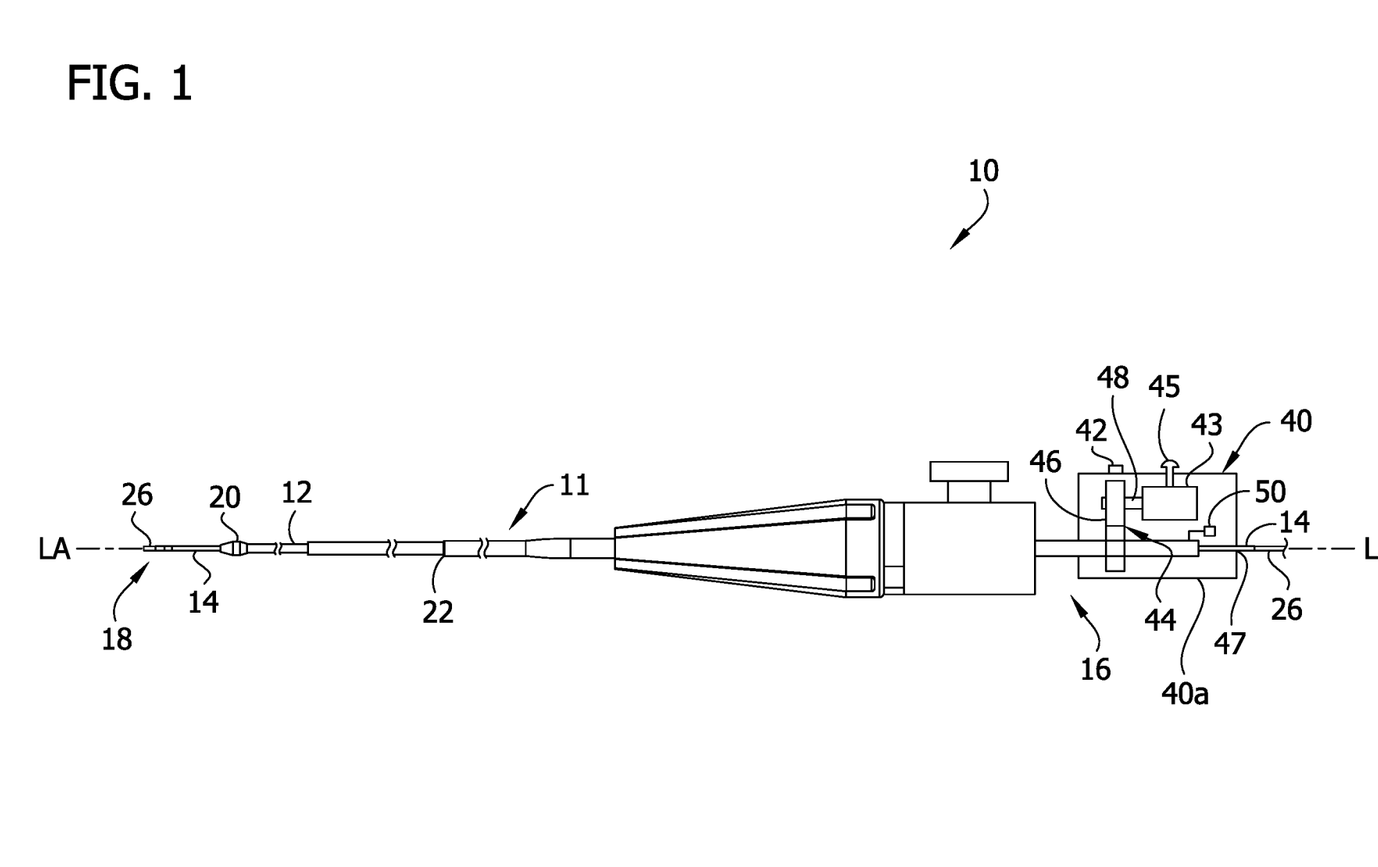
FIG. 1 is a schematic illustration of a catheter of the present disclosure.

Referring now to FIG. 1, one embodiment of a rotational tissue-removing catheter for removing tissue in a body lumen is generally indicated at reference number 10. The catheter 10 includes an elongate catheter body 11 sized for being received in a blood vessel of a subject. Thus, the catheter body 11 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
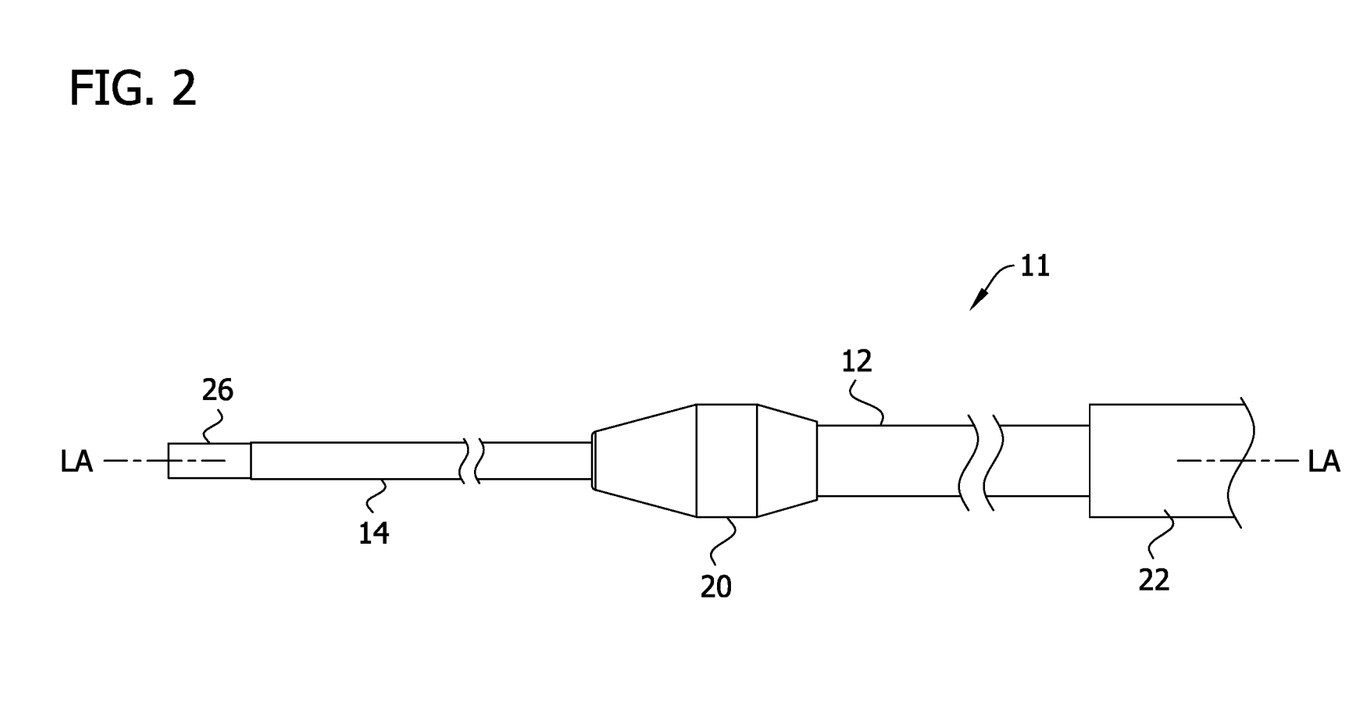
FIG. 2 is an enlarged elevation of a distal end portion of the catheter.

Referring to FIGS. 1 and 2, the catheter body 11 comprises an elongate drive shaft, e.g., drive coil 12, disposed around an elongate inner liner 14. The drive coil 12 and inner liner 14 extend along a longitudinal axis LA of the catheter body 11 from a proximal end portion 16 to a distal end portion 18 of the catheter body. An abrasive burr 20 (or other tissue-removing element) is disposed on a distal end of the drive coil 12 and is configured for rotation to remove tissue from a body lumen. The abrasive burr 20 may have an abrasive outer surface formed, for example, by a diamond grit coating, surface etching, or the like. An isolation sheath 22 (FIG. 1) is disposed around the drive coil 12. The drive coil 12 and the inner liner 14 are both configured to translate relative to the isolation sheath 22. The isolation sheath 22 isolates the body lumen from at least a portion of the drive coil 12 and inner liner 14. The space between the isolation sheath 22 and the drive coil 12 allows for the drive coil to rotate within the sheath and provides an area for saline perfusion between the sheath and drive coil. The inner liner 14 defines a guidewire lumen 24 for slidably receiving a guidewire 26 therein so that the catheter 10 can be advanced through the body lumen by traveling along the guidewire. The guidewire can be a standard 0.014-inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends all the way through the length of the inner liner 14 such that the guidewire 26 is extendable along an entire working length of the catheter 10. In one embodiment, the overall working length of the catheter 10 may be between about 135 cm (53 inches) and about 142 cm (56 inches). In use, the guidewire 26 may extend about 40 mm (1.6 inches) past a distal end of the inner liner 14.

Figure 3:
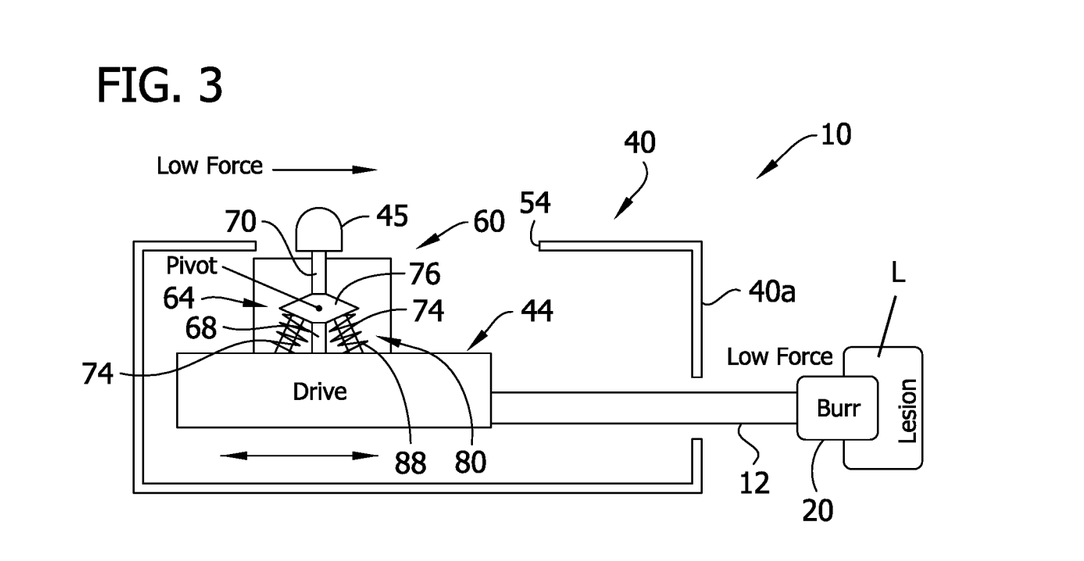
FIG. 3 is a schematic illustration of the catheter showing a linear force applied to an advancer and an articulating coupler of a linear-force indicator in a non-articulating position.
Figure 4:
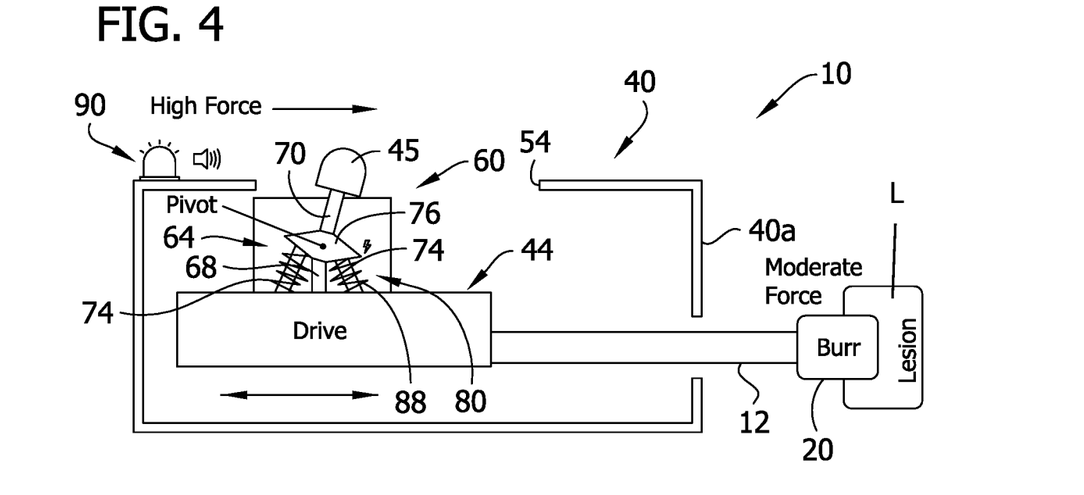
FIG. 4 is similar to FIG. 3 showing a linear force applied to the advancer and the articulating coupler in an articulating position.

Referring to FIGS. 1, 3 and 4, the catheter 10 further includes a handle, generally indicated at 40, coupled to a proximal end of the catheter body 11. The handle 40 comprises a housing 40a that supports the components of the handle. The housing 40a supports an actuator 42 (e.g., a lever, a button, a dial, a switch, or other device, as shown in FIG. 1) configured for selectively actuating a drive, generally indicated at 44, disposed in the handle to drive rotation of the drive coil 12 and burr 20 mounted at the distal end of the drive coil. The drive 44 is configured to rotate the drive coil 12 and burr 20 at speeds of greater than about 80,000 RPM. In one embodiment, as shown in FIG. 1, the drive 44 includes a motor 43 (e.g., an electric motor), a gear assembly 46 coupled to the motor, and driveshaft 48 coupled to the gear assembly and the drive coil 12. Torque is transferred from the motor 43 to the drive coil 12. The motor 43 may be powered by a battery (external or internal) or other internal or external electrical power source. Moreover, a controller 50 (FIG. 1) may be programmed to control operation of the catheter 10. The drive 44 may be of other types, such as a pneumatic drive, a hydraulic drive, or other types of drives suitable for driving rotation of the drive coil.

Referring to FIGS. 1, 3, and 4, an advancer 45 (e.g., a slide) of the handle 40 is operatively coupled to the drive 44 to selectively translate (e.g., linearly advance) the drive together with the drive coil 12 and the burr 20 to advance and retract the drive coil and burr relative to the handle and the isolation sheath 22 at the distal end of the sheath. The drive 44 may be coupled to a linear rail or other track or guide, such as illustrated in other embodiments in FIGS. 8-12. The housing 40a of the handle 40 may define a slot 54 (FIGS. 3 and 4) which limits the movement of the slide 45 relative to the handle. Thus, the length of the slot 54 determines the amount the burr 20 may be linearly advanced or displaced from the distal end of the isolation sheath 22 during debulking operation. In one embodiment, the slot 54 has a length of about 70 mm (2.8 inches), and thus the burr may be selectively advanced 70 mm (2.8 inches) between a fully retracted, proximal position to a fully advanced, distal position relative to the isolation sheath 22. A guidewire lock 47 (FIG. 1) on the handle 40 is selectively actuated to lock the guidewire 26 relative to the catheter 10 to inhibit linear movement of the catheter on the guidewire while allowing rotation of the drive coil 12 and burr 20 on the guidewire.

Referring to FIGS. 3 and 4, the catheter 10 further includes a linear-force indicator, generally indicated at 60, configured to provide an indication or feedback to the user as to the amount of linear force the user is applying to the advancer 45 during the debulking operation. During debulking and as the burr 20 is being rotated by the drive 44, the user applies a linear force to the advancer 45 to move the rotating burr against the obstruction (e.g., lesion L) in the lumen. The obstruction, in turn, applies a counterforce back to the advancer 45 and to the user. In some situations, such as when the obstruction is relatively difficult to abrade, the user may continue to apply an increasing amount of linear force to the advancer 45 in an attempt to clear the obstruction. This may lead to tissue damage and/or damage to the motor 43 if the force continues to increase. The linear-force indicator 60 is configured to indicate or provide feedback to the user when an amount of force being applied to the advancer 45 is greater than a predetermined threshold amount.

Referring still to FIGS. 3 and 4, the linear-force indicator 60 includes an articulating coupler, generally indicated at 64 (broadly, a movable coupler), operatively connecting the advancer 45 to the drive 44 such that linear force applied to the advancer is imparted to the drive through the articulating coupler. The articulating coupler 64 also provides movement of the advancer 45 relative to the drive 44 (i.e., slippage) when a linear force greater than the threshold linear force is applied to the advancer. Accordingly, when the linear force applied to the advancer 45 by the user is less than or equal to the predetermined threshold amount, then the applied linear force is applied to the drive 44 and the articulating coupler 64 does not slip (i.e., the coupler is in a non-articulated position). However, when the linear force applied to the advancer 45 by the user is more than the predetermined threshold amount, then the applied linear force is not applied to the drive 44 (or the force imparted to the drive is substantially decreased) and instead the articulating coupler 64 slips and the advancer moves relative to the drive (i.e., the coupler is moved to an articulated position). In the illustrated embodiment, the articulating coupler 64 includes a fixed arm 68 and an articulating arm 70 hingedly or pivotally connected to one another at a hinged or pivot connection. The fixed arm 68 is fixedly secured to the drive 44 (e.g., to the motor 43) and the articulating arm 70 is fixedly coupled to the advancer 45 so that the advancer is rotatable or pivotable (broadly, movable) relative to the drive 44 about a pivot axis. Other types of connections for the articulating coupler are possible.

The articulating coupler 64 is biased to its neutral or non-articulated position, such as shown in FIGS. 3 and 4, by a biasing device 74, such as one or more springs or other resilient devices. In the illustrated embodiment, the springs 74 extend between and are engageable with lever arms 76 of the articulating arm 70 and the drive 44. The lever arms 76 are pivotable about the pivot axis with the advancer 45 and are diametrically opposed relative to the pivot axis. When advancing the advancer 45 distally to move the burr 20 toward the occlusion (e.g., lesion L as shown in FIGS. 3 and 4), a distal one of the springs 74 inhibits the advancer from pivoting relative to the drive 44 about the pivot axis until and unless the linear force applied to the advancer is greater than the predetermined threshold amount, at which time the force overcomes the biasing forces of the spring 74 and the articulating coupler 64 articulates to an articulated position. This articulation is felt by the user and indicates to the user that the force applied to the advancer 45 may need to be decreased. Among other suitable parameters, the one or more springs 74 are selected to apply the appropriate amount of biasing force to correspond to the desired predetermined threshold amount of linear force. At least some of the excessive linear force applied to the advancer 45 that is greater than the threshold force is absorbed by the spring(s) 74 and not transferred to the drive or burr, thereby, in some situations, limiting excessive force being transmitted to the occlusion in the body lumen.

Figure 5:
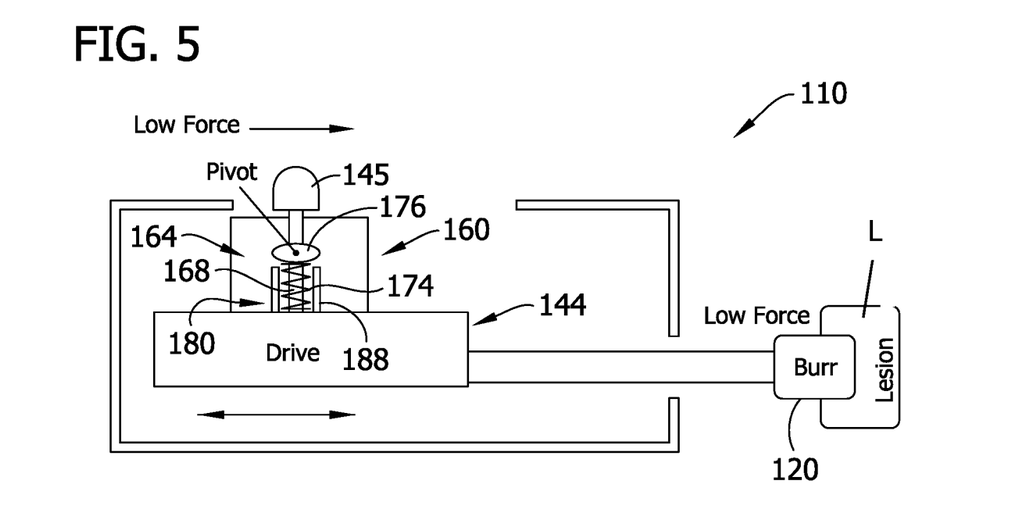
FIG. 5 is a schematic illustration of another embodiment of the catheter showing a linear force applied to an advancer and an articulating coupler of a linear-force indicator in a non-articulating position.
Figure 6:
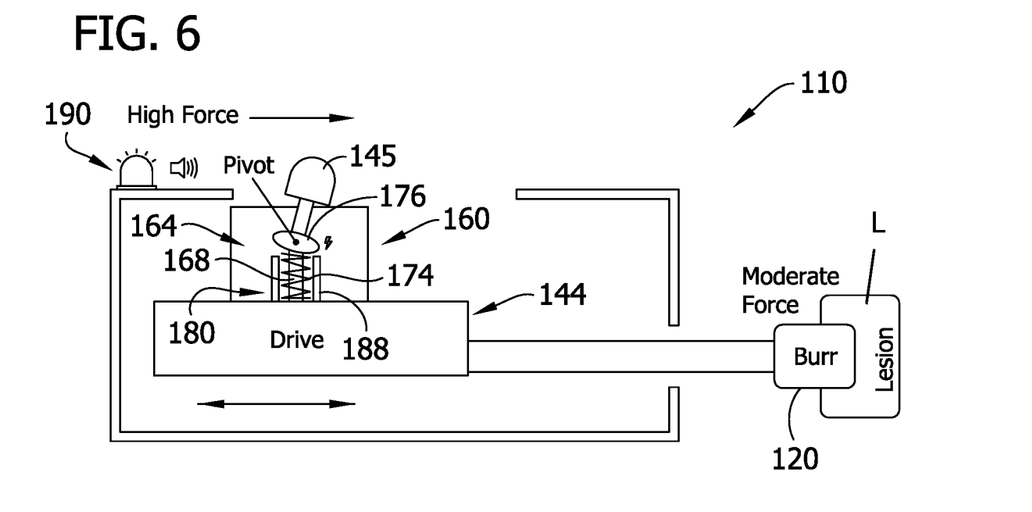
FIG. 6 is similar to FIG. 5 showing a linear force applied to the advancer and the articulating coupler in an articulating position.

The articulating coupler 64 may be biased to its non-articulated position in other ways, using other types of spring or resilient devices or in other ways. For example, another embodiment of a catheter 110 is shown in FIGS. 5 and 6. This catheter 110 is similar to the embodiment shown in FIGS. 3 and 4, with like components indicated by corresponding reference numeral plus 100. The difference between this catheter 110 and the catheter 10 is that this embodiment includes a single spring 174 (e.g., a compression spring) received on the fixed arm 168 of the coupler 164. When advancing the advancer 145 distally to move the burr 120 toward the occlusion, the spring 174 inhibits the advancer from pivoting relative to the drive 144 about the pivot axis until and unless the threshold linear force is applied to the advancer, at which time the force overcomes the biasing force of the spring and the coupler articulates to an articulated position.

In one or more embodiments, such as each of the catheters 10, 110, the linear-force indicator 60, 160 includes an electrical threshold force detector 80, 180 that is activated when the linear force applied to the advancer 45, 145 is greater than the predetermined threshold amount. It is understood that the electrical threshold force detector 80, 180 may be included independent of the articulating coupler 64, 164 and vice versa. In the illustrated embodiment, the electrical threshold force detector 80, 180 includes an electrical switch that is open when the articulating coupler 64, 164 is in the non-articulated position and closed when the articulating coupler is in the articulated position. The illustrated articulating lever arm 76, 176 forms a first electrical terminal (e.g., a positive electrical terminal) of the switch which makes electrical contact with a second electrical terminal 88, 188 (e.g., a negative electrical terminal) to close a circuit, which in turn activates an alarm 90, 190 indicating to the user that the linear force is greater than the predetermined threshold amount. The first electrical terminal may be on or part of one of lever arms 76, 176 of the coupler 64, 164. The alarm 90, 190 may be one or more of an auditory alarm (e.g., a buzzer or beeper), a visual alarm (e.g., a light, or a flashing light, such as an LED), or a haptic alarm (e.g., vibration). Closing the switch may also actuate reduction in power supplied to the motor 43, 143, including but not limited to reducing power to zero, to reduce the speed of the motor, and in turn reduce the speed of the rotating burr 20, 120. When the switch is open (e.g., reopened), the alarm 90, 190 may turn off and the power to the motor may return to normal operating parameters.

Figure 7:
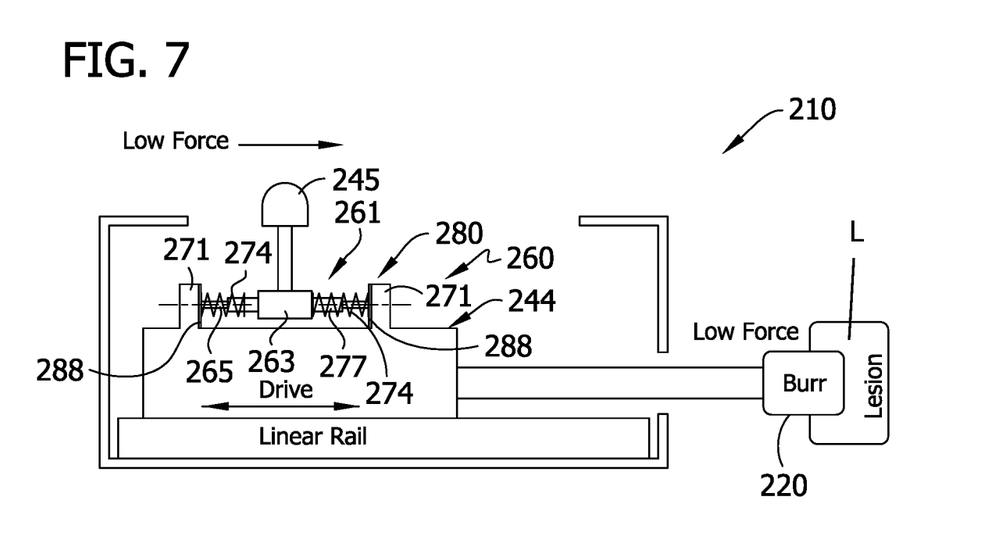
FIG. 7 is a schematic illustration of another embodiment of the catheter showing a linear force applied to an advancer and a slide coupler of a linear-force indicator in a neutral position.
Figure 8:
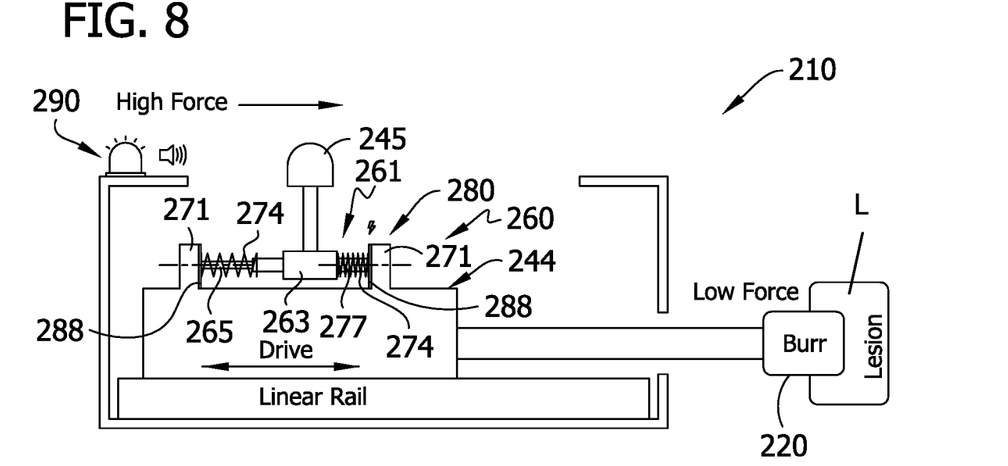
FIG. 8 is similar to FIG. 7 showing a linear force applied to the advancer and the slide coupler in a displaced position.

Referring to FIGS. 7 and 8, a catheter, generally indicated at 210, includes a different embodiment a linear-force indicator, generally indicated at 260, configured to provide an indication or feedback to the user as to the amount of linear force the user is applying to the advancer 245 during the debulking operation. This linear-force indicator 260 is similar to the first embodiment of the linear-force indicator 60, with like components indicated by corresponding reference numeral plus 200. The main difference between the first linear-force indicator 60 and the present linear-force indicator 260 is that the present linear-force indicator does not include the articulating coupler. Instead, the present linear-force indicator 260 includes a slide coupler 261 coupled to the advancer 245 to allow the advancer to move relative to the drive 244 when a linear force greater than the threshold linear force is applied to the advancer. The slide coupler 261 includes a slide 263 coupled (e.g., fixedly coupled) to a linear guide 265 that is fixedly coupled to the drive 244. The slide 263 is linearly moveable (e.g., slidable) on the liner guide 265. This embodiment also includes a linear rail, although the rail may be omitted.

A biasing device 274, such as one or more springs or other resilient devices, biases the slide coupler 261 (therefore, the advancer 245) to a neutral position, as shown in FIG. 7. In the illustrated embodiment, the biasing device includes two compression springs 274 on the liner guide 265 and disposed between opposing stops 271 and the slide 263. When advancing the advancer 245 distally to move the burr 220 toward the occlusion (e.g., lesion L as shown in FIG. 8), a distal one of the springs 274 inhibits the advancer from sliding linearly relative to the drive 244 on the linear guide 265 until and unless the linear force applied to the advancer is greater than the predetermined threshold amount, at which time the force overcomes the biasing forces of the spring 274 and the advancer moves distally on the liner guide and relative to the drive. This movement is felt by the user and indicates to the user that the force applied to the advancer 245 may need to be decreased. Among other suitable parameters, the one or more springs 274 are selected to apply the appropriate amount of biasing force to correspond to the desired predetermined threshold amount of linear force. At least some of the excessive linear force applied to the advancer 245 that is greater than the threshold force is absorbed by the spring(s) 274 and not transferred to the drive 244 or burr 220, thereby, in some situations, limiting excessive force being transmitted to the occlusion in the body lumen.

Figure 11:
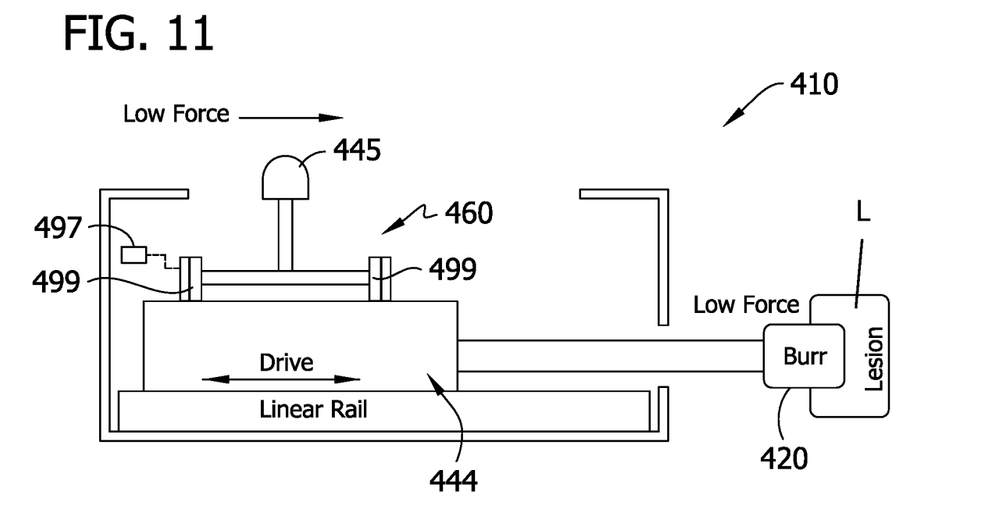
FIG. 11 is a schematic illustration of another embodiment of the catheter showing a linear force applied to an advancer, a linear-force indicator includes at least one load cell.
Figure 12:
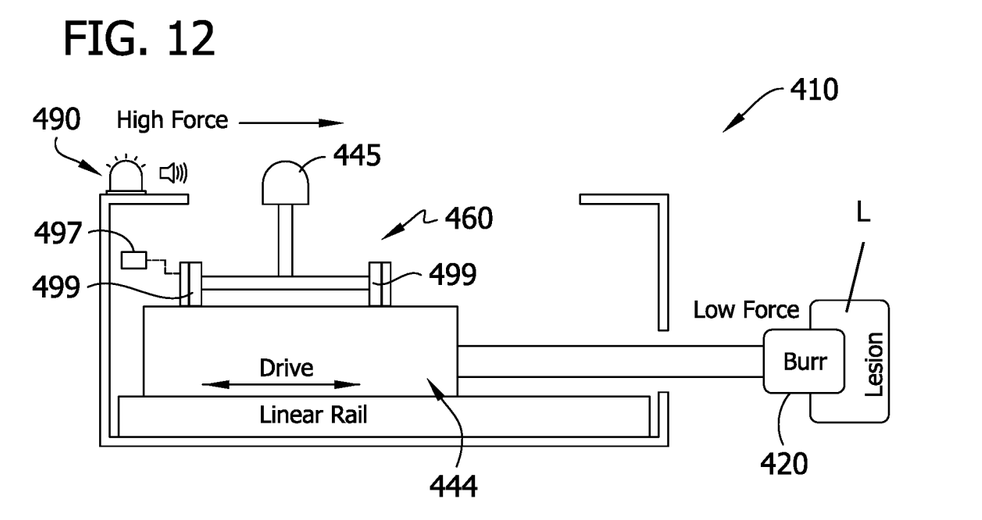
FIG. 12 is similar to FIG. 11 showing a high linear force applied to the advancer.

In the illustrated embodiment, the linear-force indicator 260 includes an electrical threshold force detector 280 that is activated when the linear force applied to the advancer 245 is greater than the predetermined threshold amount. It is understood that the electrical threshold force detector 280 may be included independent of the linear guide 265, such as shown in FIGS. 11 and 12, and vice versa. In the illustrated embodiment, the electrical threshold force detector 280 includes an electrical switch that is open when the advancer 245 is in the neutral position, and closed when the advancer is moved (i.e., displaced) to the distal (or proximal) position. The illustrated slide 263 includes a first arm or portion 277 forming a first electrical terminal (e.g., a positive electrical terminal) of the switch which makes electrical contact with a second electrical terminal 288 (e.g., a negative electrical terminal) to close a circuit, which in turn activates an alarm 290 indicating to the user that the linear force is greater than the predetermined threshold amount. The first electrical terminal 277 may be on or part of the advancer 245. The second electrical terminal 288 may be on or part of the post 271. The alarm 290 may be one or more of an auditory alarm (e.g., a buzzer or beeper), a visual alarm (e.g., a light, or a flashing light, such as an LED), or a haptic alarm (e.g., vibration). Closing the switch may also actuate reduction in power supplied to the motor of the drive 244, including but not limited to reducing power to zero, to reduce the speed of the motor, and in turn reduce the speed of the rotating burr 220. When switch is open (e.g., reopened), the alarm 290 may turn off and the power to the motor may return to normal operating parameters.

Figure 9:
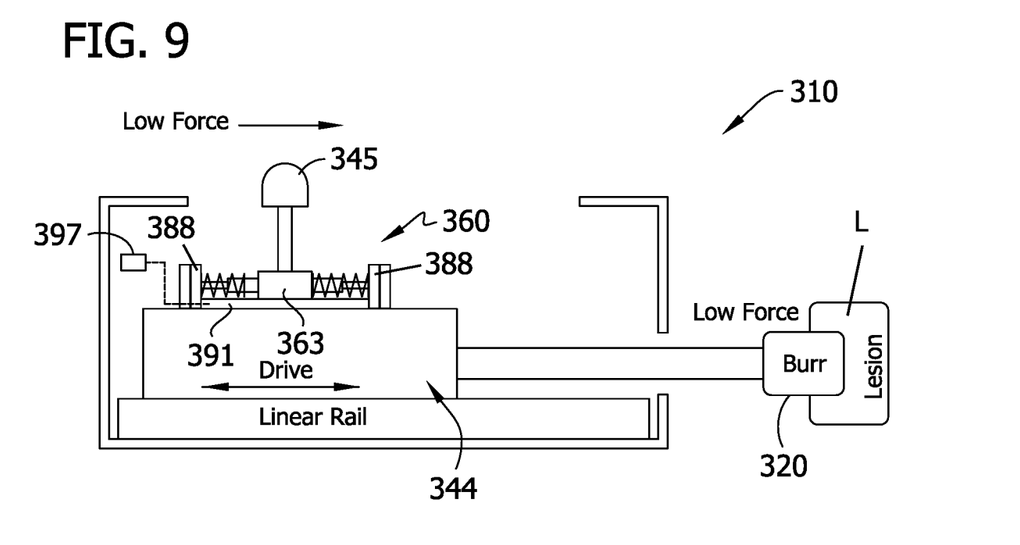
FIG. 9 is another embodiment similar to FIG. 7, but including a slide potentiometer.
Figure 10:
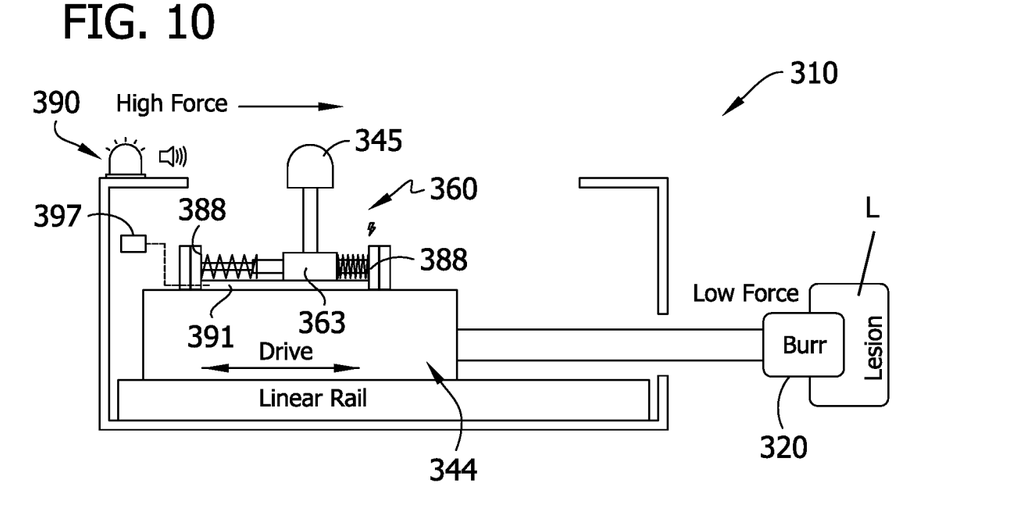
FIG. 10 is similar to FIG. 9 showing a linear force applied to the advancer and the slide coupler in a displaced position.

Referring to FIGS. 9 and 10, another embodiment of a linear-force indicator, generally indicated at 360, is similar to the linear-force indicator 260, with like components indicated by corresponding reference numeral plus 100. The present linear-force indicator 360 further includes a slide potentiometer 391 associated with the advancer 345. In particular, the slide potentiometer 391 (e.g., a slide pot) indicates the linear position of the advancer 345 (and slide 363) relative to potentiometer (and the drive 344). The linear guide may be omitted. A signal or data from the slide potentiometer 391 may be used by a controller 397 (e.g., a processor and associated memory) to determine the relative position of the advancer 345. In one example, when a relatively low or moderate force is applied to the advancer 345 such that the advancer moves relative to the drive 344 but does not move to the extent necessary to close the switch, the controller 397 may give feedback to the user, such as by reducing the speed of the burr 320 and/or giving a warning (e.g., tactile, auditory, and/or visual), based on the signal generated by the potentiometer indicating the linear position of the advancer. Thus, the slide potentiometer 391 facilitates feedback to the user before the maximum amount of linear force is reached whereby the switch is closed and the motor may be stopped and the rotational speed of the burr 320 is reduced to zero. It is understood that the switch, including the second electrical terminal 388, may be omitted, and the controller 397 may determine a threshold linear movement based on the signal generated by the side potentiometer, whereby the motor is stopped.

Referring to FIGS. 11 and 12, a catheter, generally indicated at 410, includes a different embodiment of a linear-force indicator, generally indicated at 460, configured to provide an indication or feedback to the user as to the amount of linear force the user is applying to the advancer 445 during the debulking operation. In this embodiment, the advancer 445 is not moveable relative to the drive 444, or at least any movement is nominal and/or would not be readily noticed by the user. Instead, the linear-force indicator 460 includes one or more load cells 499 (e.g., button load cells) configured to sense or detect linear force applied to the advancer 445. The load cells 499 are coupled to the drive 444 and the advancer 445, e.g., arms of the advancer, engage the load cells. Electrical signals generated by the load cells 499 may be used by a controller 497 to determine the amount of force being applied to the advancer 445 and/or determine whether a threshold amount of force is exceeded and/or control the motor based on the detected amount of force. For example, the controller 497 may be configured to selectively warn or indicate to the user (e.g., audible, tactile, and/or visual warning 490) when the force applied to the advancer is approaching a threshold amount. In one example, the controller 497 may be configured to selectively reduce the speed of the motor based on the signals generated by the load cell 499. The controller 497 may also be configured to stop the motor of the drive 444 and/or provide a suitable warning or indication when a threshold amount of force is reached or exceeded.

In an exemplary method of use, the catheter of any of the described embodiments is inserted into the body lumen (e.g., blood vessel) to deliver the tissue-removing element (e.g., burr) to the lesion L, such as shown in FIG. 13. In one example, a guidewire is delivered to the lesion L and the catheter is then slid along the guidewire to the lesion L. At the lesion, the catheter is operated to rotate the tissue-removing element to debulk the lesion. During rotation of the tissue-removing element, the advancer is moved linearly to impart linear (e.g., distal and/or proximal) movement of the tissue-removing element at the lesion. With each embodiment, the corresponding linear-force indicator provides feedback to the user indicating an amount of linear force being applied to the advancer in the manner set forth above with respect to each embodiment.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A debulking catheter for debulking a body lumen comprising:
    a catheter body configured to be inserted into the body lumen, the catheter body having a length and including a drive shaft extending along the length of the catheter body, wherein the drive shaft is configured to be rotated about its longitudinal axis;
    a tissue-removing element coupled to and configured to be rotated by the drive shaft, the tissue-removing element configured to remove tissue from the body lumen as it is rotated by the drive shaft;
    a handle operatively coupled to a proximal end of the catheter body and including:
        a drive operatively coupled to the drive shaft and configured to impart rotation of the drive shaft about its longitudinal axis,
        an advancer operatively coupled to the drive to selectively translate the drive together with the drive shaft and the tissue-removing element to linearly advance and retract the drive shaft and the tissue-removing element relative to the handle, and a linear-force indicator configured to provide feedback to a user indicating an amount of linear force being applied to the advancer, wherein the linear-force indicator includes a movable coupler operatively connecting the advancer to the drive such that linear force applied to the advancer is imparted to the drive through the movable coupler.

2. The debulking catheter set forth in claim 1, wherein the movable coupler is configured to provide movement of the advancer relative to the drive when a linear force greater than a predetermined threshold amount is applied to the advancer.

3. The debulking catheter set forth in claim 2, wherein the movable coupler comprises an articulating coupler including a fixed arm and an articulating arm pivotally connected to one another at a pivot connection.

4. The debulking catheter set forth in claim 2, wherein the movable coupler comprises a slide coupler including a linear guide and a slider slidably coupled to the linear guide.

5. The debulking catheter set forth in claim 2, wherein the movable coupler is biased to a neutral position by a resilient device.

6. The debulking catheter set forth in claim 5, wherein the resilient device comprises a spring.

7. The debulking catheter set forth in claim 5, wherein the resilient device is configured to apply a biasing force to inhibit the advancer from the moving relative to the drive via the movable coupler until and unless the linear force applied to the advancer is greater than the predetermined threshold amount, at which time the linear force overcomes the biasing force of the spring and the coupler allows the advancer to move relative to the drive.

8. The debulking catheter set forth in claim 2, wherein the linear-force indicator includes an electrical threshold force detector including an alarm that is activated if and when the linear force applied to the advancer is greater than the predetermined threshold amount.

9. The debulking catheter set forth in claim 8, wherein the alarm of the electrical threshold force detector is configured to activate in response to movement of the movable coupler from a neutral position to a displaced position.

10. The debulking catheter set forth in claim 9, wherein the electrical threshold force detector includes an electrical switch that is open when the movable coupler is in the neutral position and closed when the movable coupler is in the displaced position.

11. The debulking catheter set forth in claim 10, wherein the alarm is at least one or more of an auditory alarm, a visual alarm, and a haptic alarm.

12. A debulking catheter for debulking a body lumen comprising:
a catheter body extending distally from the handle and configured to be inserted into the body lumen, the catheter body having a length and including a drive shaft extending along the length of the catheter body, wherein the drive shaft is configured to be rotated about its longitudinal axis;
a tissue-removing element coupled to and configured to be rotated by the drive shaft, the tissue-removing element configured to remove tissue from the body lumen as it is rotated by the drive shaft;
a handle operatively coupled to a proximal end of the catheter body and including:
a drive operatively coupled to the drive shaft and configured to impart rotation of the drive shaft about its longitudinal axis,
an advancer operatively coupled to the drive to selectively translate the drive together with the drive shaft and the tissue-removing element to linearly advance and retract the drive shaft and the tissue-removing element relative to the handle, and
a linear-force indicator configured to provide feedback to the user indicating an amount of linear force being applied to the advancer, wherein the linear-force indicator includes an electrical threshold force detector including an alarm that is activated if and when the linear force applied to the advancer is greater than a predetermined threshold amount, wherein the electrical threshold force detector includes an electrical switch.

13. The debulking catheter set forth in claim 12, wherein the alarm is at least one or more of an auditory alarm, a visual alarm, and a haptic alarm.

14. The debulking catheter set forth in claim 1, wherein the tissue-removing element includes a burr.

15. The debulking catheter set forth in claim 1, wherein the drive includes an electric motor.

16. The debulking catheter set forth in claim 1, wherein the linear-force indicator is configured to selectively reduce speed of the motor based on the amount of linear force being applied to the advancer.

17. The debulking catheter set forth in claim 12, wherein the electrical switch is configured to be open when the linear force applied to the advancer is less than or equal to the predetermined threshold amount and to close when the linear force applied to the advancer is greater than the predetermined threshold amount.

18. A debulking catheter for debulking a body lumen comprising:
a catheter body extending distally from the handle and configured to be inserted into the body lumen, the catheter body having a length and including a drive shaft extending along the length of the catheter body, wherein the drive shaft is configured to be rotated about its longitudinal axis;
a tissue-removing element coupled to and configured to be rotated by the drive shaft, the tissue-removing element configured to remove tissue from the body lumen as it is rotated by the drive shaft;
a handle operatively coupled to a proximal end of the catheter body and including:
a drive operatively coupled to the drive shaft and configured to impart rotation of the drive shaft about its longitudinal axis,
an advancer operatively coupled to the drive to selectively translate the drive together with the drive shaft and the tissue-removing element to linearly advance and retract the drive shaft and the tissue-removing element relative to the handle, and
a linear-force indicator configured to provide feedback to the user indicating an amount of linear force being applied to the advancer, wherein the linear-force indicator includes a force sensor configured to sense linear force applied to the advancer, the force sensor being coupled to the advancer and the drive.

19. The debulking catheter set forth in claim 18, wherein the force sensor is movable with the advancer and the drive.

20. The debulking catheter set forth in claim 18, wherein the force sensor includes at least one load cell.

* * * * *